United States Patent [19]
Péche et al.

[11] Patent Number: 6,022,355
[45] Date of Patent: Feb. 8, 2000

[54] IMPACTION HAMMER FOR BONE CHIPS

[75] Inventors: Jean-Patrick Péche, Cergy-Pontoise;
John Andrew Storer, Bayeux;
Jean-Pierre Bree, Fontaine Etoupefour,
all of France

[73] Assignee: Benoist Girard & Cie, France

[21] Appl. No.: 09/107,226

[22] Filed: Jun. 30, 1998

[30] Foreign Application Priority Data

Jul. 2, 1997 [GB] United Kingdom .................. 9714004

[51] Int. Cl.[7] ................................................... A61B 17/58
[52] U.S. Cl. ................................................ 606/93; 606/99
[58] Field of Search ............................... 606/93, 95, 105, 606/92, 96, 99, 53, 79

[56] References Cited

U.S. PATENT DOCUMENTS

| | | | |
|---|---|---|---|
| 4,716,894 | 1/1988 | Lazzeri et al. ........................... | 128/92 |
| 5,152,792 | 10/1992 | Watkins et al. ........................... | 623/16 |
| 5,192,283 | 3/1993 | Ling et al. ................................ | 606/93 |
| 5,431,654 | 7/1995 | Nic .............................................. | 606/92 |
| 5,470,336 | 11/1995 | Ling et al. .............................. | 606/105 |
| 5,496,323 | 3/1996 | Dye ........................................... | 606/79 |
| 5,514,136 | 5/1996 | Richelsoph ................................ | 606/99 |
| 5,683,399 | 11/1997 | Jones ........................................ | 606/91 |
| 5,810,830 | 9/1998 | Noble et al. .............................. | 606/85 |

*Primary Examiner*—Michael Buiz
*Assistant Examiner*—Jonathan D. Goldberg
*Attorney, Agent, or Firm*—Lerner, David, Littenberg, Krumholz & Mentlik, LLP

[57] ABSTRACT

An apparatus for attaching an anvil or an impaction hammer to a proximal impactor to be impacted into a bone. The apparatus includes an impaction rod, the distal end of which is provided with an attachment element for releasably securing it to a securing device provided on the proximal impactor.

10 Claims, 6 Drawing Sheets

IMPACTION HAMMER FOR BONE CHIPS

BACKGROUND OF THE INVENTION

1. Field of the Invention

This invention relates to apparatus for releasably attaching an impaction hammer to a proximal impactor to be impacted into a bone.

2. Description of the Prior Art

Proximal impactors are used to impact, for example, bone chips, into, for example, the intramedullary canal of a femur into which a prosthesis is to be fitted and the impactor can have a stem which resembles the stem of the prosthesis which is to be fitted into the canal.

In known constructions the impactor has an impaction rod which is integral with it, the free end of the rod either acting as an anvil or being adapted for connection to a slap or slam hammer or similar device. Trial stems can be inserted using an impaction rod connected to a hammer with the distal end bearing against the trial stem but not connected to it.

The present invention is intended to provide apparatus which has a more universal use and can be utilized in such a way that it cannot only be used on proximal impactors but also trial stems and prostheses to be implanted. In the present invention the term "proximal impactor" will be used to not only include proximal impactors per se but also trial stems and prostheses to be implanted.

Such impactors are shown in U.S. Pat. 5,192,283 and 5,470,336.

SUMMARY OF THE INVENTION

According to the present invention, an apparatus for attaching an anvil or impaction hammer to a proximal impactor to be impacted into a bone comprises an impaction rod, the distal end of which is provided with an attachment device for releasably securing it to the securing device provided on the proximal impactor.

If desired, the proximal end of the impaction rod can also be provided with an attachment device for releasably securing it to an anvil or impaction hammer.

Preferably the locking device includes a locking element located on the impaction rod and is releasably attached thereto. Preferably, the second attachment device includes a locking device to cooperate with the securing device provided on the impactor. The locking device can include a projecting abutment which is shaped to engage beneath a cooperating securing attachment which provides the securing device on the impactor.

With this arrangement, the proximal impactor, trial stem or prosthesis can be securely attached to the hammer or anvil so that it is correctly placed to receive the results of the hammering action, but it can be easily released.

The projecting abutment is preferably adapted to rotate to engage beneath the securing abutment. Resiliently biased elements can also be included for holding the projecting abutment in position beneath the securing abutment. Preferably the locking element is in the form of a rotatable sleeve which surrounds the impactor rod.

The device for releasably attaching the locking element can comprise a radially extending shaped slot which engages a retaining member on the impaction rod. Alternatively the radially extending slot can be provided on the impaction rod and the retaining member on the locking element.

Thus, the radially extending shaped slot can have a circumferentially extending component into which the retaining member can be rotated to attach and lock the locking element to the impaction rod.

Resiliently biased elements can also be provided for holding the retaining member in the rotated position in the slot. The proximal impactor can be in the form of a trial stem and include means to receive a ball end, or can include a ball end, so that it can be used as a trial stem.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 4 is a cross-sectional end elevation on the line 4—4 of FIG. 3 showing part of the construction;

DESCRIPTION OF THE PREFERRED EMBODIMENT

Figure 1:
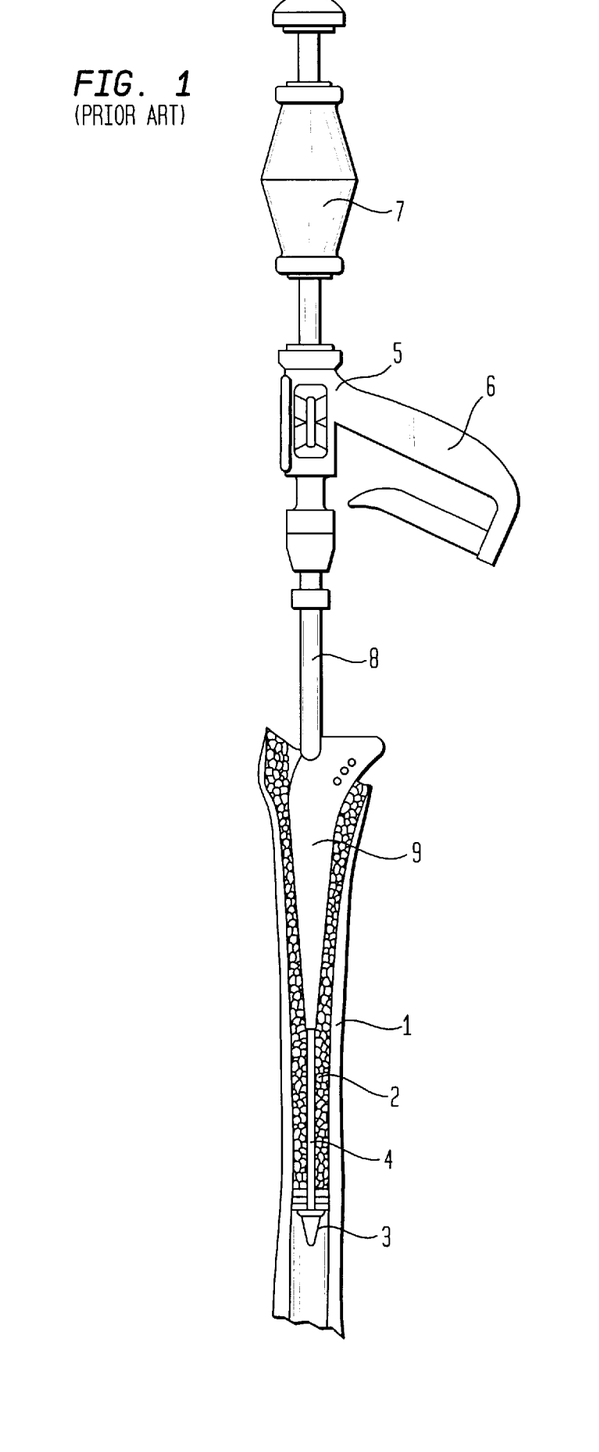
FIG. 1 shows a prior art construction in which an impaction hammer is used to drive a proximal impactor into position.

FIG. 1 shows a prior art construction for impacting a proximal impactor into bone chips in the intramedullary canal of a femur.

The femur 1 is filled with impacted bone chips 2 which are located in place by a bone plug 3. A guide wire 4 is provided onto which the various parts can be threaded in known manner. The impaction hammer 5 has a handle 6 and a slap hammer 7 for providing the impaction effect. The hammer is attached to an impaction rod 8 which is integral with a proximal impactor 9.

A first embodiment of the present invention is shown in FIGS. 2 to 7 and comprises apparatus for releasably attaching an impaction hammer, for example, of the kind shown in FIG. 1, to a proximal impactor, a trial stem or a prosthesis to be impacted into bone chips as described above.

The construction will be described with regard to use with a proximal impactor which, because of the unique construction of the present invention, can also be used as a trial stem.

Figures 2, 3, 4, 5, 6, 7:
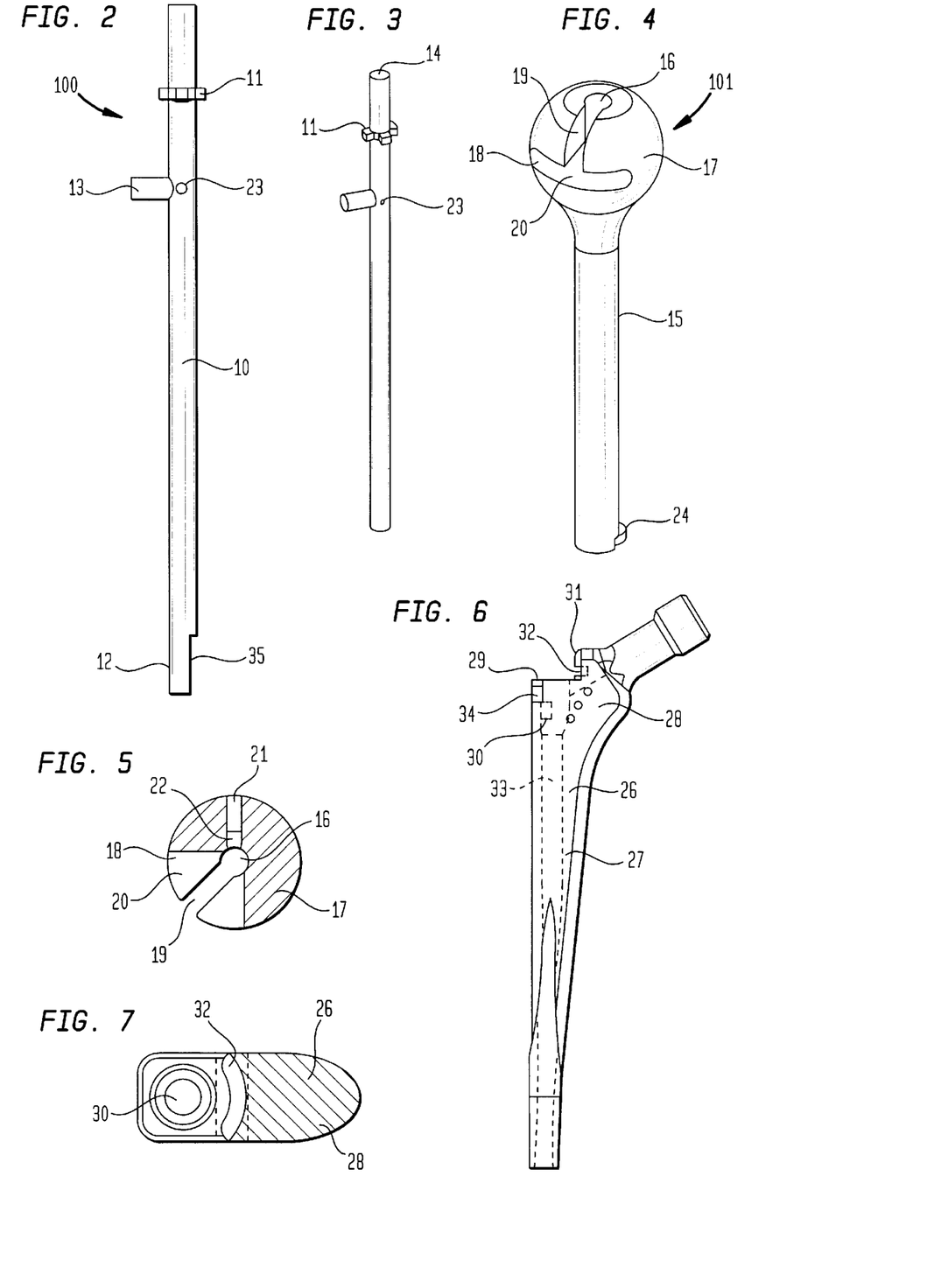
FIG. 2 is a side elevation of an impaction rod which forms part of the apparatus of the present invention.
FIG. 3 is an isometric view of the rod shown in FIG. 1.
FIG. 4 is an isometric view of a locking element for use with the rod shown in FIGS. 2 and 3.
FIG. 5 is a side elevation of a trial stem incorporating part of the invention.
FIG. 6 is a cross-sectional plan view on the line 6—6 of FIG. 5.
FIG. 7 is an isometric view of the stem shown in FIGS. 5 and 6.

The apparatus 100 comprises an impaction rod 10, as shown in FIG. 2 and FIG. 3, provided with conventional means for attachment to an impaction hammer of the kind shown in FIG. 1. The attachment means comprises a cruciform shaped fitting 11 which is of known type and will not be described in further detail. The distal end 12 of the impaction rod 10 is adapted to engage the proximal end of the impactor shown in FIGS. 6 and 7 in the manner to be described hereunder. The rod 10 also carries retaining means in the form of a cross member 13 which in the preferred embodiment is in the form of a pin which is shaped to engage a locking element shown in FIG. 4.

The impaction rod is also provided with a bore 14 to receive a guide wire of known type.

A locking element 101 for use with the rod 10 comprises a sleeve 15 having a hollow bore 16 which is shaped to slide over the rod 10 and allow it to rotate. The proximal end of the sleeve 15 has an enlarged head 17 in which is located a double keyhole slot 18 which is formed by a radially extending shaped slot 19 which has a circumferentially extending component 20 which extends on either side of the slot 19 and is most clearly shown in FIG. 5. The enlarged head 17 is also provided with a radial bore 21 in which is located a spring loaded plunger 22 which in the preferred embodiment is a resiliently biased pin which can engage depressions 23 on each side of the impaction rod adjacent the cross member 13 and which can cooperate with the plunger 22 when the parts are assembled together to retain the sleeve 15 in predetermined locking positions which are at 90° to each other. The distal end of the sleeve 15 is provided with a projecting abutment 24.

A proximal impactor in the form of a trial stem 26 which forms part of the invention is shown in FIG. 6 and comprises a stem portion 27 and a head portion 28, the proximal end of which is provided with a flat surface 29 and a bore 30 which is of a diameter to accept the distal end 12 of the rod 10 as a push fit. Also located at the proximal end of the stem 26 is a projecting securing abutment 31 which is formed as a slot 32 which is shaped and dimensioned to receive the projecting abutment 24 on the sleeve 15.

The trial stem 26 also has a bore 33 to receive a guide wire in known fashion and a set screw 34 is provided, the inner end of which projects into the bore 30 where it can cooperate with a flat 35 formed on the distal end of the impaction rod 10.

The parts are assembled together by first sliding the sleeve 15 over the rod 10 from the distal end of the rod until the cross member 13 passes down the slot 19. The assembly is now placed on the trial stem 26 with the distal end 12 of the rod 10 in the bore 30, the set screw 34 engaging the flat 35 to prevent rotation of the rod 10. The sleeve 15 is now rotated with the cross member 13 passing along the slot 18 and the abutment 24 rotates until it engages in the groove 32 on the trial stem. The plunger 22 now acts to hold the retaining member, in the form of the cross member 13, in position in the slot 18 and the impaction rod is securely held onto the trial stem 26. The assembly can now be fitted to the hammer in the usual way.

In order to disassemble the apparatus, it is merely necessary to rotate the sleeve 15 against the action of the plunger 22 until the cross member 13 is in alignment with the slot 19. In this position the abutment 24 is released from the slot 32 and the parts can be taken apart.

The sleeve and impaction rod can, however, be held together if desired after removal from the stem 26 by rotating the sleeve further until cross member 13 enters the other side of the slot 18 where the second depression 23 engages the plunger 22 to hold the parts together.

Figure 8:
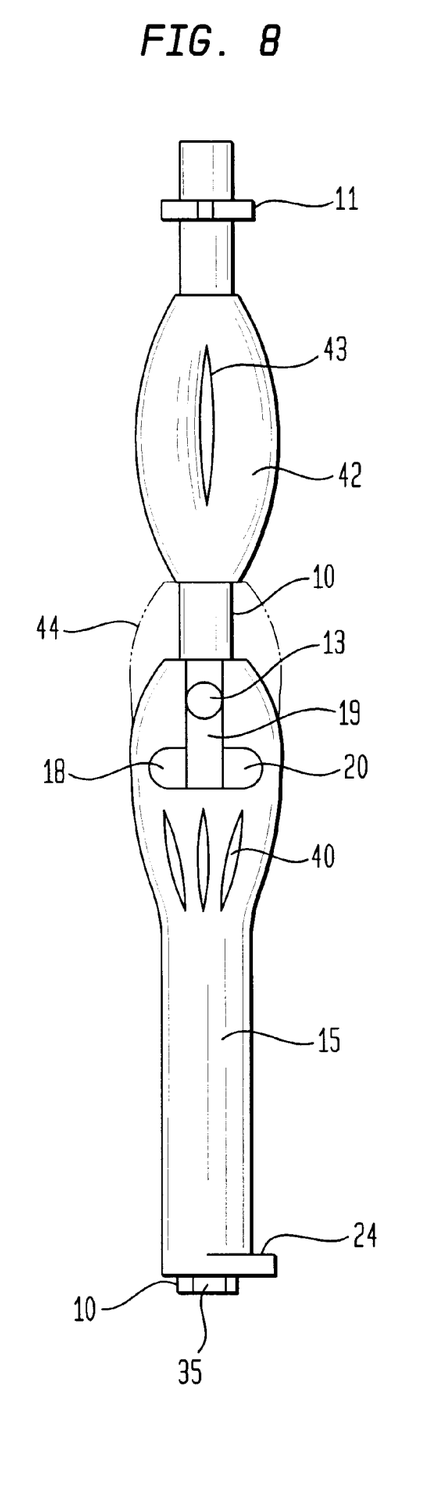
FIG. 8 is a side elevation of a second embodiment.

FIG. 8 shows a construction which is generally similar to that shown in FIGS. 2 to 6 and the same reference numerals are used to indicate similar parts. In this construction however, the sleeve 15 is of a different shape and carries serrations 40 to assist in its manipulation. A hand grip 42 is also rigidly attached or provided on the impaction rod 10 and this also carries serrations 43.

This embodiment acts in a similar manner to the construction shown in FIGS. 2 to 6. In FIG. 8 the sleeve 15 is shown in position ready for attachment to the trial stem 26. The distal end of the rod 10 is pushed into the bore 30 and at the same time the sleeve 15 rises until the cross member 13 is aligned with the slot 18. The sleeve can now be rotated so that the abutment 24 locks in the groove 32. This raised position of the sleeve is indicated by broken lines 44.

The arrangement is such that the proximal end of the sleeve 15 now bears against the distal end of the hand grip 42 so that when the impaction hammer is operated, impaction loads are not only communicated through the impaction rod 10, but also through the hand grip 42 and the sleeve 15 to the trial stem 26.

Figure 9:
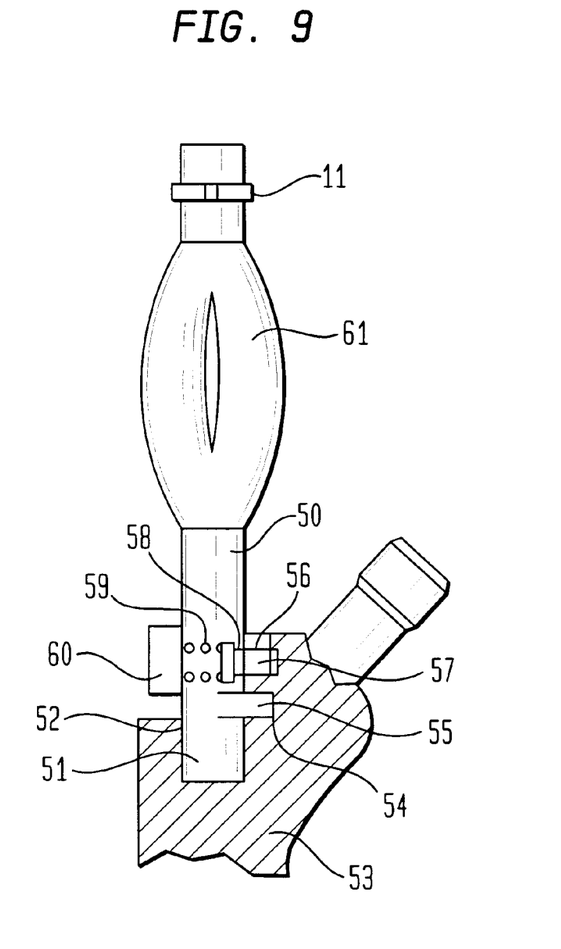
FIG. 9 is a part cross-sectional side elevation of a further embodiment of the invention.

The constructions described above have been found to operate successfully, but if desired, a simplified construction as shown in FIG. 9 can be employed. In this arrangement an impaction rod 50 is provided with attachment means 11 of the kind described with regard to the earlier embodiments for attachment to an impaction hammer. The distal end 51 of the rod 50 is dimensioned to be a push fit in a bore 52 in a trial stem 53. The trial stem is also provided with a slot 54 into which a projecting abutment 55 provided on the impaction rod 50 can engage when the rod is rotated. Thus, the construction is somewhat similar to the arrangement provided on the construction shown in FIGS. 2 to 8 for the engagement of the sleeve 15.

The trial stem 53 is also provided with a blind bore 56 which can receive a resiliently biased pin 57. This pin, which is located in a bore 58 in the rod 50, is biased by a compression spring 59 toward a position in which it projects from the rod and the other end of the pin is provided with an enlarged head 60 to enable the pin to be retracted when the head is pulled to compress the spring 59.

With this construction the distal end of the impaction rod 50 is first placed in the bore 52 in the trial stem 53 and is then rotated so that the abutment 55 engages into the slot 54. At the same time the pin 57 is either held in a retracted position or is forced into a retracted position by engaging the surface of the stem 53 until it is aligned with the bore 56. The pin then passes into the bore 56 due to the effect of the compression spring 59. The impaction rod 50 is now firmly locked onto the trial stem 53 ready for impaction to take place.

In order to remove the impaction rod 50 from the stem 53 it is merely necessary to retract the pin 57 against the action of the spring 59 by pulling on the enlarged head 60 and the rod 50 can then be rotated to disengage the abutment 55 from the slot 54.

In order to assist operation of the device, a hand grip 61 is provided on the impaction rod 50.

FIGS. 10 to 16 show another form of the present invention and the same reference numerals are used to define similar parts to those shown in FIGS. 1 to 9. In this construction an impaction rod 10 is again provided with conventional means for attachment to an impaction hammer which includes a cruciform shaped fitting 11.

Figure 13:
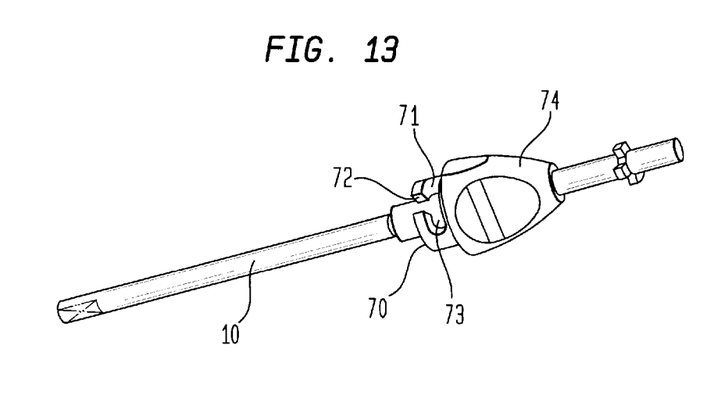

The distal end 12 of the rod is again adapted to engage the proximal end of the impactor and the rod carries retaining means which, in this construction, are provided by an enlarged portion 70 in which is located a double keyhole slot 71 and which comprise a radially extending shaped slot 72 which has a circumferentially extending component 73 which extends on either side of the slot 72 and which is most clearly shown in FIG. 13. It will be appreciated that this slot is similar to keyhole slot 18 provided in the locking element shown in FIG. 4. The enlarged portion 70 is also provided with a shaped end portion 74.

Figures 10, 11, 12:
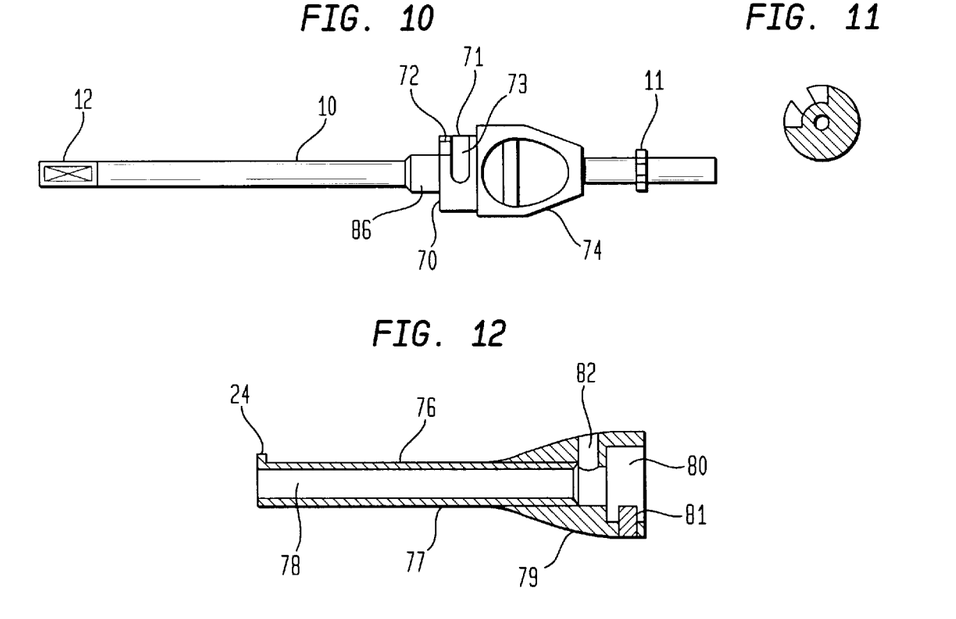
FIG. 10 is a side elevation of an impaction rod for another alternate construction.
FIG. 11 is a cross-sectional end view on the line XI—XI of FIG. 10.
FIG. 12 is a cross-sectional side elevation of a locking element for use with the rod shown in FIGS. 10 and 11.
Figure 12A:
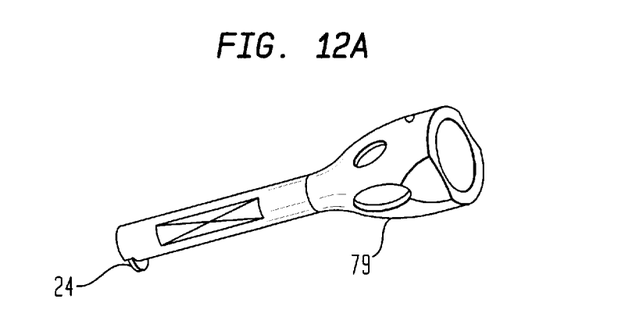
FIGS. 12A and 13 are an isometric views of the rod shown in FIGS. 10 and 11 and the locking element shown in FIG. 12 ready for assembly.

A locking element 76 is provided for use with the rod 10 and this comprises a sleeve 77 having a hollow bore 78 which is shape to slide over the rod 10. The proximal end of the locking element has an enlarged portion 79 in which is provided an enlarged socket 80, the dimensions of which are arranged so that it is an easy sliding fit over the enlarged portion 70 of the rod 10. Projecting radially inwardly is an abutment pin 81 which is dimensioned and adapted to pass into the keyhole slot 71 when the parts are assembled. A radially extending bore 82 carries a mounting 83 in which is located a spring loaded plunger 84 and retaining ball 85 which are adapted to engage depressions (now shown) on a boss 86 provided on the rod 10.

The distal end of the locking element is again provided with a projecting abutment 24 similar to that shown in FIG. 4.

With this construction the retaining member is provided on the locking element and is in the form of the pin 81.

It will be appreciated that the keyhole slot and retaining member are thus reversed when considered in relation to the construction shown in FIGS. 1 to 6 but the operating action is similar.

Once again, the parts are assembled together by first sliding the sleeve 77 over the rod 10 from the distal end of the rod until the pin 81 passes down the slot 72. The assembly is now placed on the trial stem 26 with the distal end of the rod in the bore 30 in exactly a similar manner to that described with regard to FIGS. 1 to 6. The sleeve 77 is now rotated so that the pin 81 passes along the slot 72 and the abutment 24 rotates until it engages in the groove 32 on the trial stem. The resiliently biased ball 85 now acts to hold the retaining member in position in the slot 77 and the impaction rod is securely held onto the trial stem 26. The assembly can now again be fitted to the hammer in the usual way.

Disassembly of the apparatus is the reverse to assembly.

Once again the sleeve and impaction rod can be held together if desired after removal from the stem 26 by rotating the sleeve further until the pin 81 enters the other side of the slot and when the second depression (not shown) in the boss 86 engages the retaining ball 85 to hold the parts together.

Figure 14:
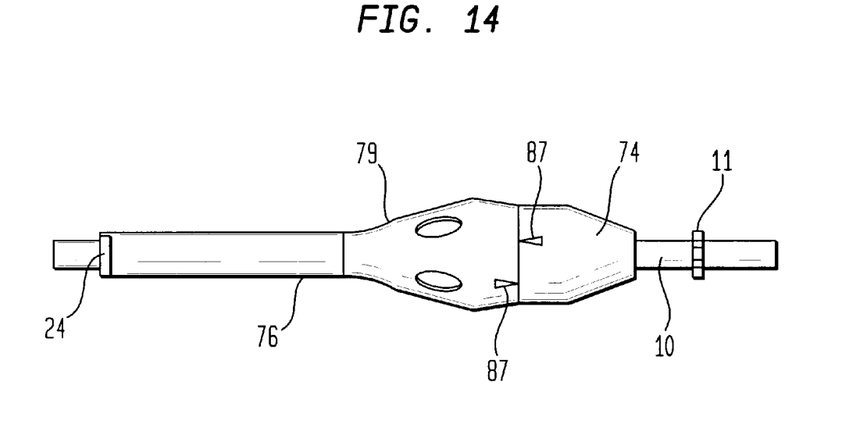
FIG. 14 is a side elevation of the parts shown in FIG. 12 assembled together.
Figure 15:
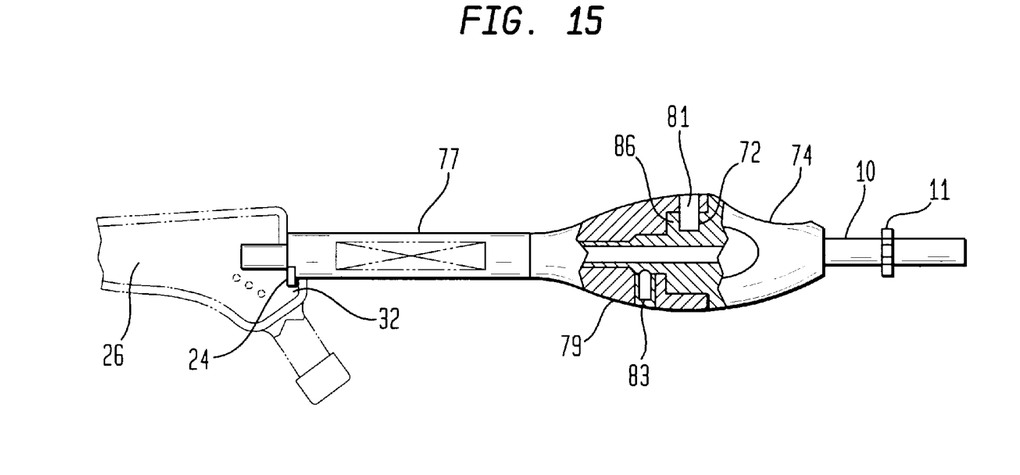
FIG. 15 is a side elevation in part cross-section showing the rod and locking element shown in FIGS. 10 to 14 assembled onto a trial stem or proximal impactor.
Figure 16:
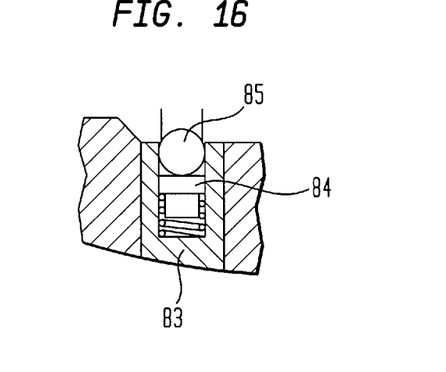
FIG. 16 is a cross-sectional detail view of part of the assembly shown in FIG. 15.

In order to clearly indicate the positions of the parts, markers 87, as shown in FIG. 14, are provided. These indicate the relative rotary positions of the rod 10 and the locking element 76, the position in which the pin 81 and slot 71 are in alignment indicating the disengagement position of the two parts.

In all the constructions described above, the impaction rod 10 is shown with conventional means for attachment to an impaction hammer, but it will be appreciated that the same means can alternatively be used for attachment to an anvil. In certain circumstances some surgeons prefer to use such a device which basically comprises an anvil head which can be struck by a mallet, hammer or similar device wielded by the surgeon. Some surgeons feel that they have more control using this kind of device for applying a force to the impact rod. When using such an anvil, it can be removably attached to the rod 10 in a similar manner to the impaction hammer 5 shown in FIG. 1.

Figure 17:
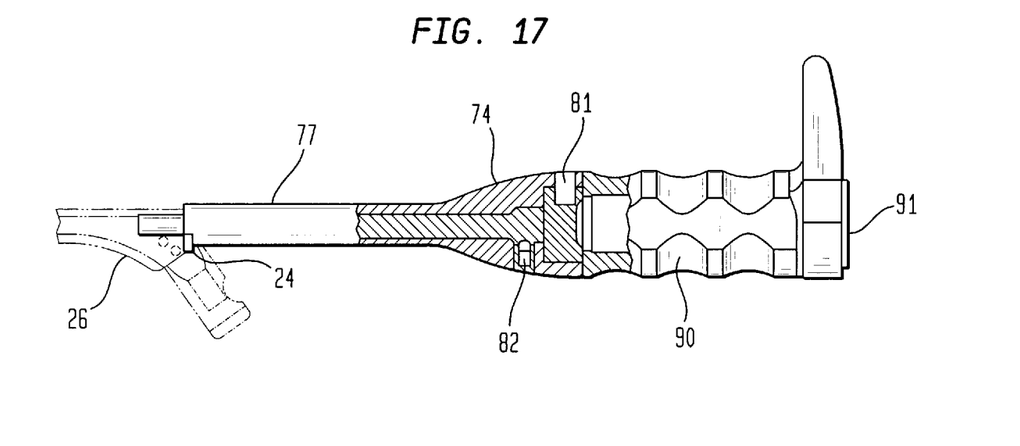
FIG. 17 is a part cross-sectional view of the assembly shown in FIG. 15 applied to an anvil.
Figure 18:
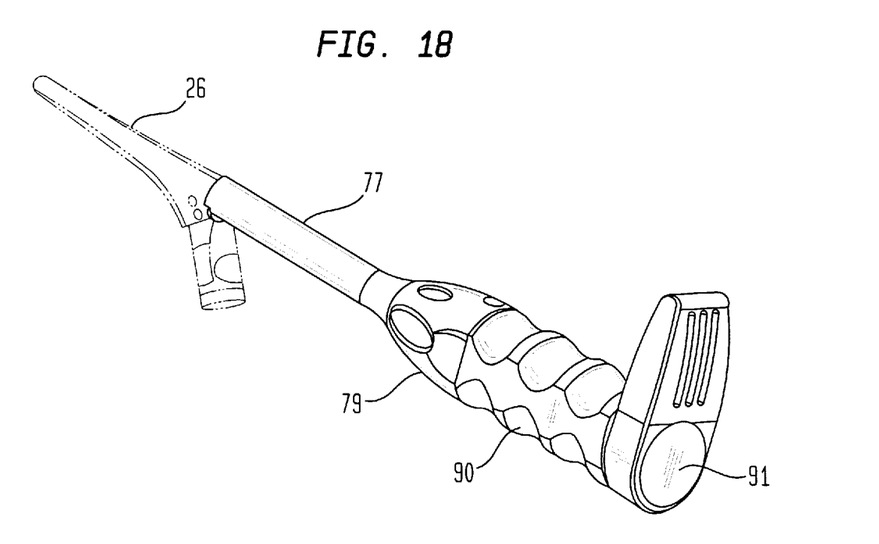
FIG. 18 is an isometric view of the construction shown in FIG. 17.

If desired, however, an impact anvil can be formed as part of the impact rod 10 and FIGS. 17 and 18 show such a construction. In this arrangement the same reference numerals are used to indicate the same parts as those shown in FIGS. 10 to 15 but the proximal end and end portion 74 of the impaction rod are replaced by a hand grip 90 embodying an anvil 91. If desired such a hand grip and anvil, or even anvil alone, can be formed on the proximal end of the impaction rod shown in FIGS. 1 to 9 to replace the proximal end of the rod and the cruciform shaped fitting 11.

It will be appreciated that the above constructions are merely examples of means for releasably securing the impaction rod to a proximal impactor and other arrangements could be employed.

While several examples of the present invention have been described, it is obvious that many changes and modifications may be made thereunto, without departing from the spirit and scope of the invention.

I claim:

1. An apparatus for impacting material in a bone canal with an anvil or impaction hammer comprising:
   an impactor for insertion into said bone canal with a proximal end and a distal end and having a recess formed in said proximal end including a slot extending into said proximal end and opening into said recess;
   an impaction rod having a distal end for insertion into said recess and having a pin extending in a direction transverse to a longitudinal axis of said rod; and
   a sleeve at least partially surrounding said rod for sliding engagement therewith both longitudinally and rotationally, said sleeve having a slot for engaging said pin on said rod and having a distal end with a projection formed thereon, the projection engaging said slot in said recess upon insertion and rotation of said sleeve within said recess.

2. The apparatus as set forth in claim 1 wherein said impactor includes a longitudinal axis aligned with said longitudinal axis of said impaction rod wherein said proximal recess has a bore extending in a distal direction along said axis, said bore for receiving the distal end of said rod.

3. The apparatus as set forth in claim 1 wherein said slot extends in a direction transverse to said longitudinal axis of said impactor.

4. The apparatus in claim 1 wherein said sleeve is at least partially tubular in form having a bore completely surrounding said impaction rod and is coaxial therewith and wherein said projection extends in a direction transverse to said longitudinal axis of said rod.

5. The apparatus of claim 4 wherein said sleeve has an enlarged portion which includes said slot for engaging said pin, said slot having a T-shape.

6. The apparatus of claim 5 wherein said T-shaped slot includes a portion aligned with said longitudinal axis of said impaction rod and perpendicular to a crossbar of said T-shaped slot, said portion having an open end at a proximal portion of said sleeve for receiving said pin on said rod.

7. The apparatus as set forth in claim 6 wherein said sleeve includes a resilient plunger communicating with said bore thereon for engagement with said rod to lock said pin in a selected position along the crossbar of said T-shaped slot.

8. The apparatus of claim 6 wherein when said impaction rod is mounted in said bore and said pin is located at a first end of the crossbar of said T-shaped slot, said projection engages said slot in said proximal recess and when said pin is located at a second end of said T-shaped slot, the projection is disengaged from said slot in said recess and said plunger is engaged with said rod, locking said pin in said slot to prevent disassembly of said sleeve and said impaction rod.

9. An apparatus for impacting material in a bone canal with an anvil or impaction hammer comprising:

an impactor for insertion into said bone canal with a proximal end and a distal end and having a recess formed in said proximal end including a slot extending into said proximal end and opening into said recess;

an impaction rod having a distal end for insertion into said recess and having a pin extending in a direction transverse to a longitudinal axis of said rod;

a sleeve at least partially surrounding said rod for sliding engagement therewith both longitudinally and rotationally, said sleeve having a slot for engaging, said pin on said rod and having a distal end with a projection formed thereon, the projection engaging said slot in said recess upon insertion and rotation of said sleeve within said recess; and said sleeve having an inner bore thereon arranged along said axis, said slot being T-shaped with a crossbar of said T-shaped slot having a first end and a second end, said crossbar receiving said pin so that rotation of said sleeve about said impaction rod moves said projection into engagement with said slot in said recess and the pin of said rod into engagement with the first end of said crossbar.

10. The apparatus as set forth in claim 9 wherein said sleeve includes a resilient plunger communicating with said bore for engagement with said rod when said pin is at the second end of said crossbar to lock said pin in said slot of said sleeve.

* * * * *

UNITED STATES PATENT AND TRADEMARK OFFICE
CERTIFICATE OF CORRECTION

PATENT NO.    : 6,022,355
DATED         : February 8, 2000
INVENTOR(S)   : Péche et al.

It is certified that error appears in the above-identified patent and that said Letters Patent is hereby corrected as shown below:

Column 2, line 47, cancel the word "an".
Column 8, line 8, cancel the ",".

Signed and Sealed this

Twentieth Day of February, 2001

Attest:

NICHOLAS P. GODICI

Attesting Officer    Acting Director of the United States Patent and Trademark Office